(12) United States Patent  
Auclair et al.

(10) Patent No.: US 9,968,316 B2
(45) Date of Patent: May 15, 2018

(54) HIGH-FREQUENCY ANTI-SCATTER GRID MOVEMENT PROFILE FOR LINE CANCELLATION

(71) Applicant: GENERAL ELECTRIC COMPANY, Schenectady, NY (US)

(72) Inventors: Colin Auclair, Buc (FR); Carlos Martinez Ferreira, Paris (FR); Remy Andre Klausz, Neuilly sur Seine (FR); Henri Souchay, Versailles (FR); Mathias Cisaruk, Paris (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 229 days.

(21) Appl. No.: 15/082,812

(22) Filed: Mar. 28, 2016

(65) Prior Publication Data

US 2016/0206259 A1 Jul. 21, 2016

Related U.S. Application Data (63) Continuation-in-part of application No. 13/329,356, filed on Dec. 19, 2011, now Pat. No. 9,770,215.

(30) Foreign Application Priority Data

Dec. 29, 2010 (FR) ..................... 10 61334
Feb. 29, 2016 (FR) ..................... 16 51669

(51) Int. Cl.
*A61B 6/00* (2006.01)
*A61B 6/06* (2006.01)

(52) U.S. Cl.
CPC ............ *A61B 6/4291* (2013.01); *A61B 6/502* (2013.01); *A61B 6/5252* (2013.01); *Y10T 29/49826* (2015.01)

(58) Field of Classification Search
CPC .......... A61B 6/06; A61B 6/4291; A61B 6/502
See application file for complete search history.

(56) References Cited

U.S. PATENT DOCUMENTS 5,666,395 A    9/1997   Tsukamoto et al.
6,304,632 B1  10/2001   Rick et al.
(Continued)

FOREIGN PATENT DOCUMENTS

EP    1126289 A2   8/2001
JP    3755144 B2   3/2006
(Continued)

OTHER PUBLICATIONS

Joseph et al., "The Effects of Sampling on CT Images", Computerized Tomography, vol. No. 04, Issue No. 03, pp. 189-206, 1980.

(Continued)

*Primary Examiner* — Don Wong (57) ABSTRACT

A process for deploying an anti-scattering grid in a mammograph is provided. The mammograph comprises a radiation source configured to emit radiation for taking mammographic images of a patient, a radiation detector comprising a network of sensors arranged periodically with a first pitch, and an anti-scattering grid arranged between the source and the detector, the anti-scattering grid comprising radiation adsorbing strips arranged parallel to each other and distributed periodically with a second pitch. The process comprises: displacing the anti-scattering grid relative to the detector or displacing the detector relative to the anti-scattering grid during emission of radiation; adapting the second pitch to the first pitch, wherein displacement is perpendicular to the direction of the strips of the anti-scattering grid, the strips being arranged parallel to a side of the anti-scattering grid positioned against the patient, and altering the positions of the return points between successive periods of the displacement motion.

20 Claims, 4 Drawing Sheets

(56) References Cited

U.S. PATENT DOCUMENTS 6,333,990 B1    12/2001    Yazici et al.
6,771,738 B2     8/2004    Miotti et al.
7,050,618 B2     5/2006    Belykh et al.
7,142,705 B2    11/2006    Inoue et al.
7,336,811 B2     2/2008    Takeo

FOREIGN PATENT DOCUMENTS

WO    03045246 A2    6/2003
WO    2007061152 A1  5/2007

OTHER PUBLICATIONS

Seibert et al., "X-Ray Scatter Removal by Deconvolution", The International Journal of Medical Physics Research and Practice, vol. No. 15, Issue No. 4, pp. 567-575, Jul. 1988.

Gauntt et al., "Grid Line Artifact Formation: A Comprehensive Theory", The International Journal of Medical Physics Research and Practice, vol. No. 33, Issue No. 6, Part1, pp. 1668-1677, 1654, Jun. 2006.

Yoon et al., "Reduction of a Grid Moiré Pattern by Integrating a Carbon-Interspaced High Precision X-Ray Grid with a Digital Radiographic Detector", Medical Physics, vol. No. 34, Issue No. 11, pp. 4092-4097, Nov. 2007.

Unofficial English Translation of French Search Report and Written Opinion issued in connection with related FR Application No. 0858109 on Mar. 31, 2009.

HIGH-FREQUENCY ANTI-SCATTER GRID MOVEMENT PROFILE FOR LINE CANCELLATION

CROSS-REFERENCE TO RELATED APPLICATIONS

This application is a continuation-in-part of co-pending U.S. patent application Ser. No. 13/329,356, filed Dec. 19, 2011, which claims priority to French Patent Application Serial No. 1061334, filed Dec. 29, 2010, now French Patent No. 1061334. This application further claims priority to French Patent Application Serial No. 1651669, filed Feb. 29, 2016. All of the patent applications and patents listed above are hereby incorporated by reference in their respective entireties.

BACKGROUND

The present disclosure is generally related to the field of medical imaging, and more particularly the field of radiography. Embodiments of the present invention relate to the field of the deploying anti-scattering grids used to improve radiographic images by filtering the photons scattered by the organ under study, and keeping only the photons emitted by the source. Embodiments of the present invention can be utilised within the scope of mammography, and more particularly within the scope of breast tomosynthesis, which takes a series of frames at different angles to produce a 3D image of the object being studied.

Anti-scattering grids are used widely in radiography devices to eliminate the effects generated by the parasitic scattering of some photons taking place in the organ studied by said devices. These grids filter photons scattered by the organ being studied and mainly keep only photons actually originating from the radiation source of the radiography device, thus improving the contrast of the obtained images.

Figure 1:
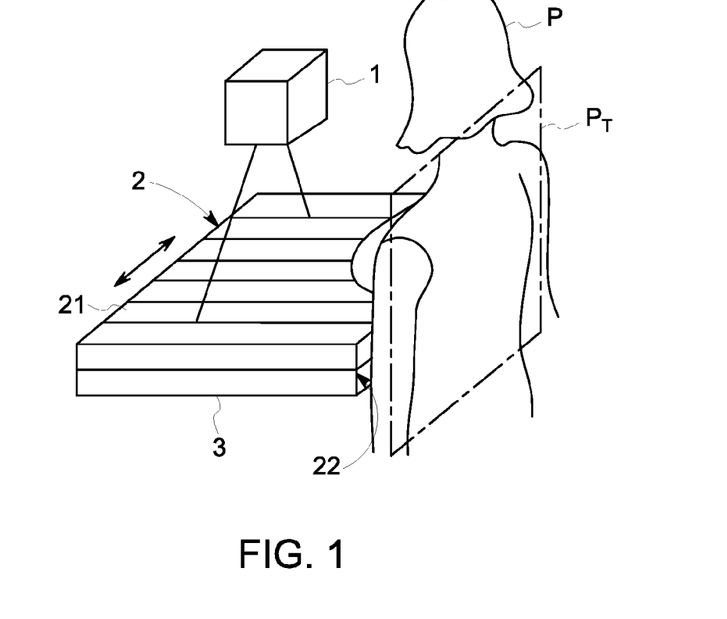
FIG. 1 illustrates a process for deploying an anti-scattering grid according to the prior art.

In FIG. 1, a conventional use of an anti-scattering grid 2 is illustrated. The grid 2 is placed between a body part to be studied of a patient P who is irradiated by a radiation source 1, and a radiation detector 3 comprising a network of sensors 31 (illustrated in FIG. 3) distributed periodically with a period $p_d$ (later called the pitch of the detector).

The assembly made up of the grid and the detector is positioned according to a plane perpendicular to the plane PT of the torso of the patient. By way of non-limiting example, illustrated in FIG. 1, the patient P can be standing and the grid and the detector are then on a horizontal plane, the walls of the grid and of the detector in contact with the patient being tangential to the plane $P_T$.

The grid 2 is generally constituted by alternating radio-opaque and radio-transparent strips 21, the axes of strips 21 being parallel and distributed periodically, with a pitch $p_g$ between two radio-opaque strips so that the scattered photons are absorbed by the radio-opaque strips and the photons coming directly from the source 1 are transmitted to the detector 3 of the radiography device. In some embodiments, known as "focused grids," the plane of the strips perpendicular to the plane of the detector is slanted to match the beam divergence from the focal spot to the detector at a specific source-to-detector distance.

One drawback of using such grids is that an image of the radio-adsorbing strips of the grid appears on the detector. Also, alternating strips can cause interference figures, or moiré effect, on the detector and deteriorate the quality and legibility of the image obtained.

Figure 2A:
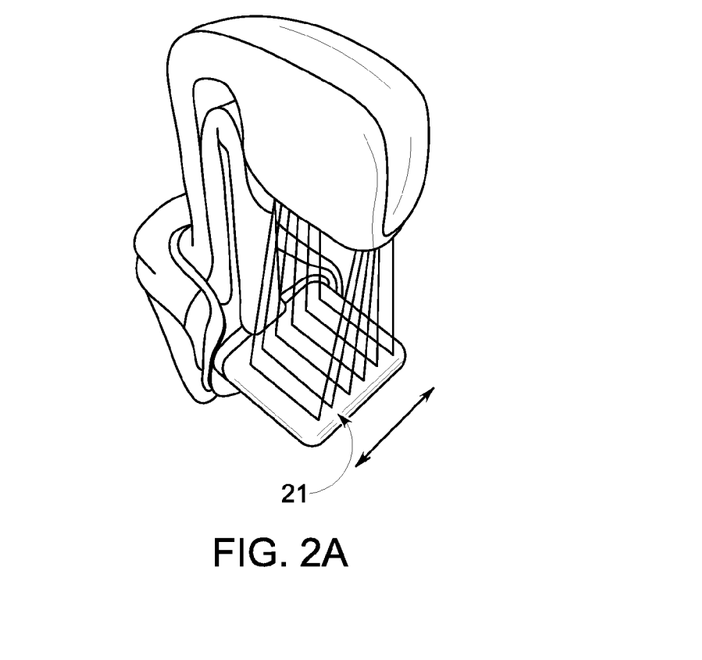
FIG. 2A illustrates a traditional mammography device using an anti-scattering grid.

For erasing the image of the radio-adsorbing strips, commonly termed "erasing the grid lines" and similar phrases, a solution known in mammography and schematically illustrated in FIGS. 1 and 2A is used, consisting of animating the grid 2 by any vibration movement perpendicular to the direction according to which the strips 21 extend.

Figure 2B:
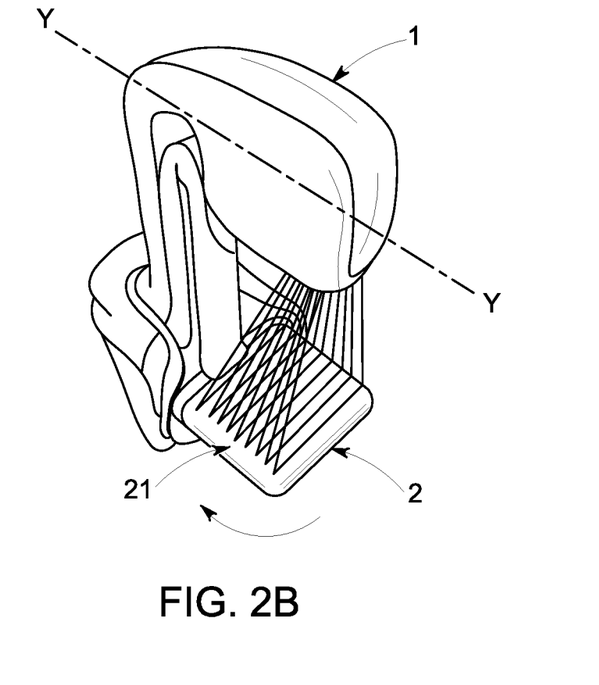
FIG. 2B illustrates a tomosynthesis device deploying an anti-scattering grid.

In terms of breast tomosynthesis, acquiring a 3D image of the object means acquiring a series of images of the object according to different relative angular positions between the source, the detector, and the body part under study. Since it is desired to reconstruct tomographic images of the whole breast, including of areas as close as possible to the chest wall it is required that all successive images (known as "frames") acquired during the tomographic sweep contain information relative to all points of the volume of the breast. By simple geometric construction, the natural consequence is that most images should be taken with the source in the plane of the chest wall. Therefore the movement of the source between images should reside in this plane, and consequently the grid focusing line as well. For this to occur, the radiation source 1 is pivoted about an axis Y-Y, illustrated in FIG. 2B, perpendicular to the plane of the torso of the patient P.

In standard static imaging the orientation of the grid is generally with the grid strips and the focusing line perpendicular to the chest wall. In breast tomosynthesis the grid strips have to be oriented parallel to the chest wall, i.e., pivoted 90° relative to the usual orientation.

Figure 3:
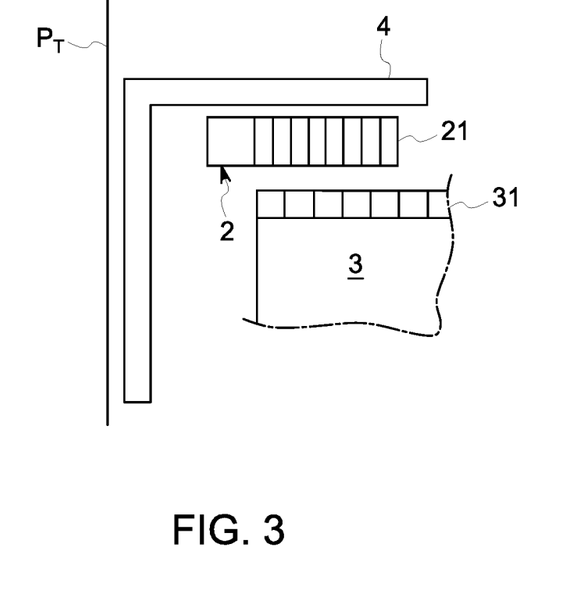
FIG. 3 illustrates a configuration of an anti-scattering grid on a radiation detector.

For reasons associated with bulk, and limited space between the chest wall of the patient and the wall of the detector/grid assembly, as illustrated in FIG. 3, it then becomes difficult to execute displacement of the grid 2 perpendicularly to the direction of the strips.

A further problem with this displacement, if periodic in nature, is the creation of shadowing and decreased contrast caused by the return points of the radio-adsorbing grid strips. More particularly, return points arise as a function of the amplitude and frequency of the movement of the grid and are defined as the point at which the direction of travel alters from one direction to a second (typically opposite) direction. Return time is defined as the time centered on the return point in which grid movement slows down, stops, and resumes in the opposite direction with a comparable speed.

Current patterns of grid movement which use a fixed frequency or amplitude for grid movement increase the risk of making shadows from the grid strip at the return points visible in the images. A solution would be to reduce the return time to a degree where its impact becomes negligible on the strip visibility. However, by way of an illustrative example, for a 2 mm amplitude periodic movement and 50 ms exposure time this would require accelerations as high as 30 g, which cannot be achieved at acceptable bulk and cost with currently available technologies.

In effect, in reference to FIG. 3, the detector 3 and the anti-scattering grid 2 are located under a cover 4 likewise supporting the breast of the patient throughout examination. Legislation imposes that the distance between the chest wall of the patient and the closest sensors 31 of the detector 3 be less than 5 mm.

This interval must also comprise the thickness of the cover 4 and the inactive edge of the grid 2 where no strips are present. Given these elements, the space remaining for the grid 2 to move is less than 2 mm.

Since the movement required to erase the image of the grid is of the order of 10 mm, due to spacing constraints this movement cannot occur along an axis perpendicular to the plane of the torso $P_T$ of the patient.

Solutions adopted in breast tomosynthesis in the prior art to eliminate the image of the grid on the detector propose adapting the pitch of the grid $p_g$ to the pitch of the detector $p_d$, so that the pitch of the grid $p_g$ is, for example, equal to a multiple of the pitch $p_d$ of the detector.

Another solution presented in document FR 2,939,019 consists of adapting the pitch of the grid to the Nyquist frequency of the detector then digitally filtering the image of the grid on the detector.

As outlined above, none of these solutions gives a completely satisfactory result. In particular, even if the grid is no longer visible on the frame, a moiré effect remains, linked to interference between the strips of the grid and the network of sensors of the detector.

What is needed, therefore, is an apparatus and process for making an image with a grid having strips parallel to the chest wall of the patient P, while at the same time avoiding any residual image of the grid strips or resulting moiré patterns in the image.

BRIEF DESCRIPTION OF THE INVENTION

Embodiments of the present invention provide a process and device for deploying an anti-scattering grid, applicable to mammography and to breast tomosynthesis, which eliminates both the image of the grid on the detector, residual shadows from return points, and the residual moiré effects. The invention further decreases the acceleration stress on the grid, allowing for a wider range of materials to be chosen.

According to one embodiment of the present invention, a process for deploying an anti-scattering grid in a mammograph is provided. The mammograph comprises a radiation source configured to emit radiation for taking mammographic images of a patient, a radiation detector comprising a network of sensors arranged periodically with a first pitch, and an anti-scattering grid arranged between the source and the detector, the anti-scattering grid comprising radiation absorbing strips arranged parallel to each other and distributed periodically with a second pitch. The process comprises: displacing at least one of the anti-scattering grid relative to the detector and displacing the detector relative to the anti-scattering grid during emission of radiation; wherein displacement is perpendicular to the direction of the strips of the anti-scattering grid, the strips being arranged parallel to a side of the anti-scattering grid positioned against the patient; and wherein the locations of the return points are changed between successive cycles of the displacement motion.

According to another embodiment of the present invention, a mammograph is provided. The mammograph comprises a radiation source configured to emit radiation for taking mammographic images of a patient. The mammograph further comprises a radiation detector comprising a network of sensors arranged periodically with a first pitch and an anti-scattering grid arranged between the source and the detector, the anti-scattering grid comprising radiation absorbing strips arranged parallel to each other and distributed periodically with a second pitch. The mammograph comprises at least one actuator configured to displace the anti-scattering grid relative to the detector or displace the detector relative to the anti-scattering grid during emission of radiation, wherein displacement is perpendicular to the direction of the strips of the anti-scattering grid, the strips being arranged parallel to a side of the anti-scattering grid positioned against the patient; and wherein the locations of the return points are changed between successive cycles of the displacement motion.

BRIEF DESCRIPTION OF THE DRAWINGS

Other characteristics, aims and advantages of the present invention will emerge from the following detailed description, with respect to the attached figures given by way of non-limiting examples and in which.

DETAILED DESCRIPTION OF THE INVENTION

Figure 4:
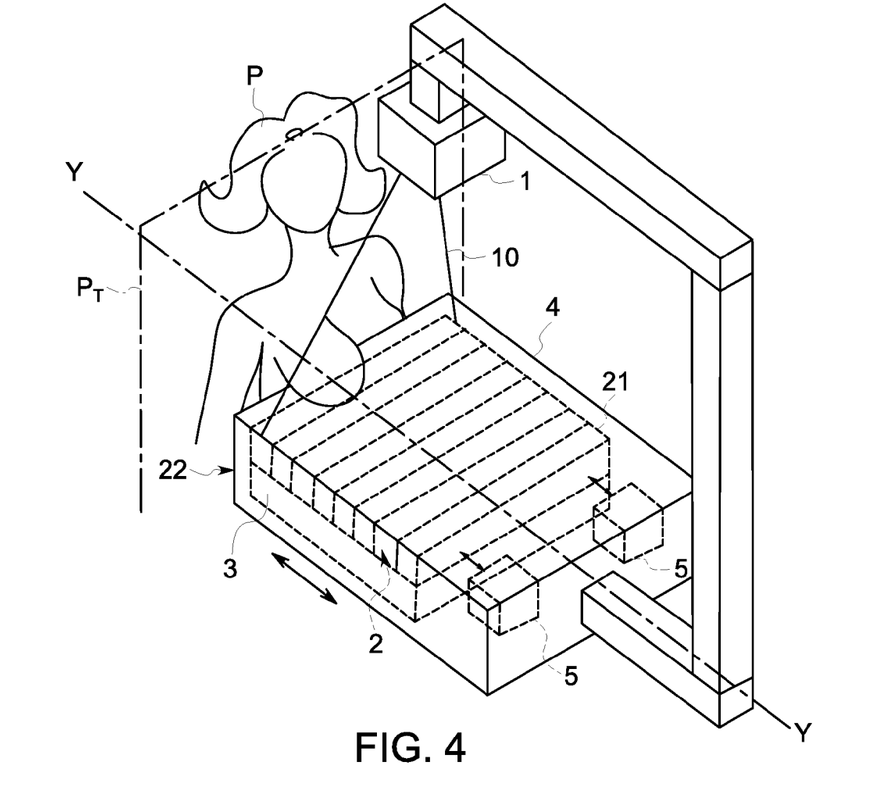
FIG. 4 schematically illustrates creation of a mammograph according to an embodiment of the present invention.

In reference to FIG. 4, a mammograph is illustrated comprising a radiation source 1, for example of X-ray type, emitting radiation 10 designed to illuminate the breast of a patient P of whom images are to be taken during a pause time T. The radiation transmitted then reaches a detector 3 made up of a network of sensors 31 (Shown in FIG. 3) distributed periodically with a pitch $p_d$ of the detector, of the order of 20 to 200 µm.

An anti-scattering grid 2 is interposed between the source 1 and the detector 3, more precisely between the breast of the patient P and the detector 3, so as to stop radiation scattered by the breast of the patient P not coming directly from the source 1.

This anti-scattering grid 2 is placed immediately above the detector 3, and is protected by means of a cover 4. This cover also forms a support for the breast of the patient to be examined.

The grid 2 comprises alternating radio-opaque strips 21, for example constituted by metal, and radio-transparent strips 21, which can be cavities in the grid, the strips 21 being parallel and distributed periodically with a pitch $p_g$ between two radio-opaque strips, This pitch $p_g$ is for example adapted to that of the detector, that is, it can be a multiple of the pitch $p_d$ of the detector 3, for example equal to the pitch $p_d$ of the detector 3, or even be a multiple of the Nyquist frequency of the detector 3. For example, a pitch of the grid $p_g$ may be about 100 µm. The grid 2 may have a thickness of the order of about 1 mm to 3 mm, and sides of a length of the order of about 18×24 to 24×30 cm. In an example embodiment, the ratio of the detector pitch to the grid pitch is 1.5.

The strips 21 of the grid are oriented according to a direction parallel to one side 22 of the grid 2 against which the patient P can be positioned. As such, the source 1 is capable of pivoting about an axis, Y-Y, thus enabling the capture successive frames to construct 3D images.

The mammograph also comprises one or more actuators 5, whereof two are illustrated by way of non-limiting example in FIG. 4. This actuator or these actuators 5 permit relative movement between the grid 2 and the detector 3 explained herein below, by shifting the grid 2 relative to the detector 3 or alternatively by shifting the detector 3 relative to the grid 2, or simultaneously shifting both relative each other, over a time T corresponding at least to the exposure time of the patient P.

The actuator or the actuators 5 can be located on the same side of the grid 2, and located under, as it is, under the cover 4 which holds the grid and the detector.

Given the abovementioned spread of less than 2 mm between the edge of the grid 2 and the internal edge of the cover 4 at the side 21 against which the patient P can be positioned, the actuator or the actuators 5 can be located to the side opposite the patient chest wall. This also reduces added bulk caused by addition of this actuator or these actuators 5.

Figure 6:
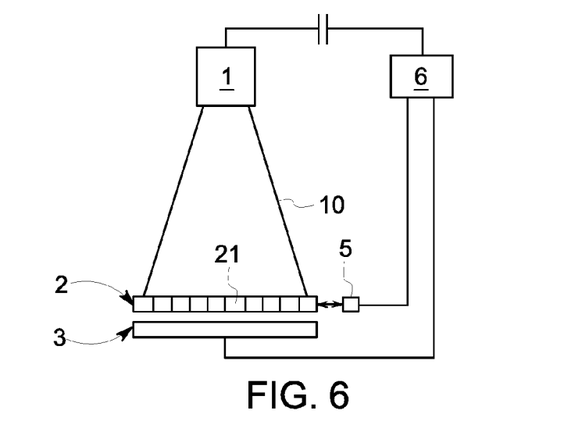
FIG. 6 schematically illustrates a mammograph according to an embodiment of the present invention.

In reference to FIG. 6, the source 1, the actuator or the actuators 5 and the detector 3 are connected to a control and processing unit 6 which manages both the source 1 and the actuator or the actuators 5 and also ensures acquisition and processing of images, if needed.

Relative movement between the grid 2 and the detector 3 eliminates the moiré on the detector 3 by varying the phase of the latter during the exposure time T. For this, it comprises at least one component according to a direction perpendicular to the direction in which the strips 21 of the grid 2 extend. In addition, the amplitude of the movement of the grid 2 or of the detector 3 according to this component, irrespective of its nature, should be at least one grid pitch $p_g$ in every sensor 31 of the detector 3 throughout exposure time T.

According to a first embodiment of relative displacement between the grid 2 and the detector 3, the actuator or the actuators 5 can be piezoelectric motors. In this case, they shift the grid 2 or the detector 3 according to a translation movement along an axis perpendicular to the direction of the strips 21, that is, perpendicularly to the side 21 of the grid 2 against which the patient P can be positioned.

Figure 5A:
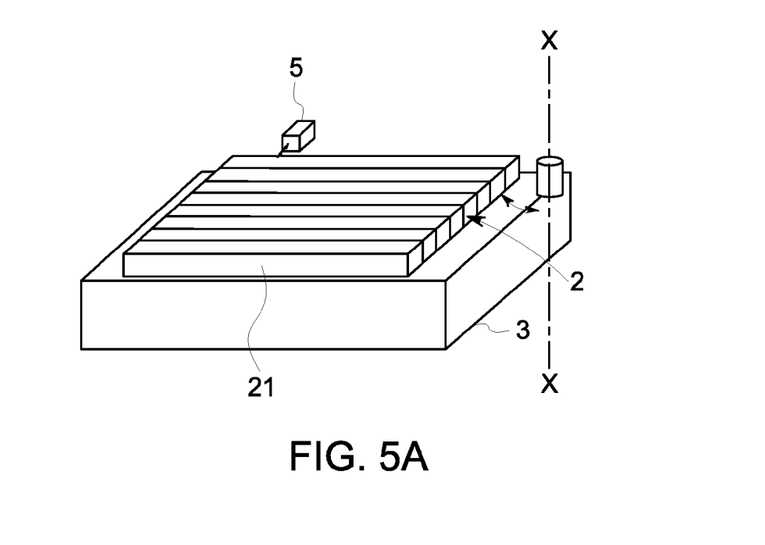
FIG. 5A illustrates an example for deploying relative movement according to an embodiment of the present invention.
Figure 5B:
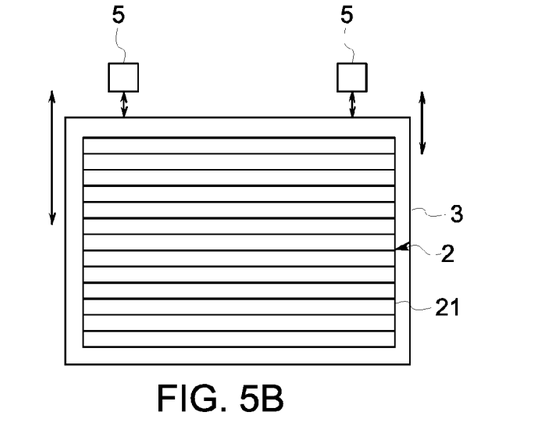
FIG. 5B illustrates, in plan view, an example for deploying relative movement according to an embodiment of the present invention.

In a variant illustrated in FIG. 5B, the mammograph comprises just one motor 5 connected to a reducer and a cam for executing angular displacement, in its plane, of the grid 2 or of the detector 3 about an axis X-X illustrated in the figure, by means of rotation whereof the centre is located outside the grid 2, respectively the detector 3. This variant has the advantage of using just one motor, reducing usage costs of such a mammograph.

In this case, the amplitude of rotation corresponding to the amplitude of displacement is adapted as a function of the distance between the grid 2 (or the detector 3), and the centre of rotation. This embodiment modifies the moiré phase non-uniformly during the exposure time T, another way of deleting the moiré figures.

As per another variant illustrated in FIG. 5B, the mammograph comprises at least two motors 5, actuating the grid 2—respectively the detector 3—at different speeds and preferably non-multiple integers such that they are desynchronised, which also modifies the moiré phase non-uniformly during the exposure time T.

In another embodiment, the motor or motors 5, displacing the grid 2 or the detector 3 can be stepper motors, electromagnets, voice coils, linear motors, and the like. In this case, one or more of these either singly or in multiple combinations thereof provide the displacement motion for grid 2.

In the case of more than one motor arranged in series or parallel, different types of technologies can be combined, such as a stepper motor for the main periodic movement and, in the transmission between this motor and the grid, an additional piezoelectric actuator generates the random variation of the return point.

The movement of the grid 2—respectively of the detector 3—whereof especially some components such as its displacement speed and its amplitude, is dependent of the exposure time or pause time T.

The total amplitude of the movement of the grid 2—respectively of the detector 3—can thus be equal to k times the pitch of the grid $p_g$, k being an integer or a semi-integer between 1 and 50, depending on the pitch $p_g$ of the grid.

In the case of a grid pitch equal to 100 microns, k can be between 1 and 20 inclusive, corresponding to displacement of the grid 2—respectively of the detector 3—by amplitude between around 100 µm and 2 mm.

Thus, displacement of minimal amplitude can be done in the abovementioned small space (of the order of 2 mm) between the cover 4 and the grid 2.

This movement, in conjunction with adaptation of the pitch of the grid $p_g$ to the pitch of the detector $p_d$, eliminates the image of the grid on the detector, as well as the residual moiré effects. Movement of only the grid 2—respectively of the detector 3—by likewise minimal amplitude would not eliminate the image of the grid 2. Further enhancing the movement by also altering the return points of the grid motion results in increased image contrast and clarity as shadows from the return points are removed from the image.

The speed v of the grid 2—respectively of the detector 3—enabling this displacement during the exposure time T can be constant and equal to v=Δx/T where Δx is the total amplitude of the displacement of the grid.

Alternatively, the grid 2—or the detector 3, if required—can be animated by oscillatory movement which can be periodical or not.

In the case of periodical movement, the speed v of the grid 2—respectively of the detector 3—can be constant throughout each half period.

The amplitude of the movement of the grid 2—respectively of the detector 3—on oscillation can be equal to k times the pitch of the grid, k being an integer or a semi-integer between 1 and 50, depending on the pitch $p_g$ of the grid.

In the case of a grid pitch equal to 100 microns, k can be between 1 and 20 inclusive, corresponding to displacement of the grid 2 by amplitude between around 100 µm and 2 mm.

Because of this mammograph and the process for deploying the grid which is executed, neither the image of the grid on the detector, shadows from return points, nor does any moiré effect appear on the images obtained.

Figure 7:
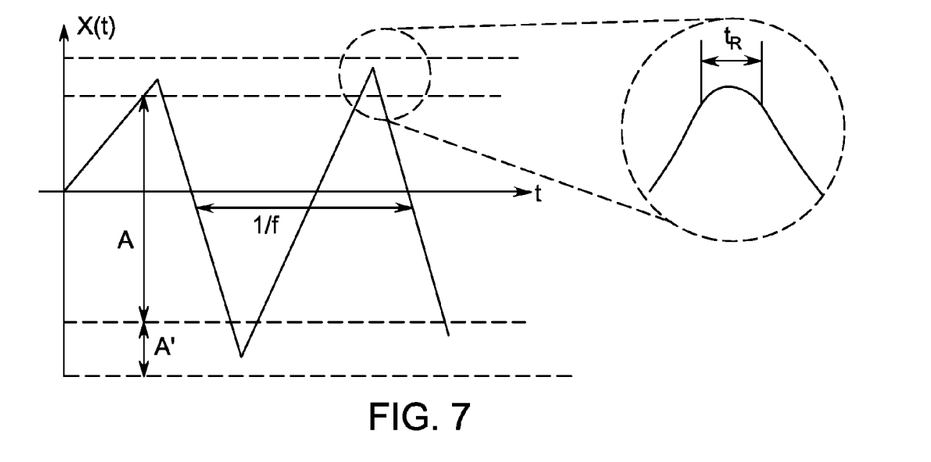
FIG. 7 represents an illustration of a displacement motion profile for an embodiment whereby displacement motion amplitude is derived from a randomized triangular periodic wave pattern, resulting in altered return point positions. Wherein X(t) is grid position as a function of time (t), with grid movement period 1/f, amplitude A, and a zone wherein the amplitude can vary A'. The response time, $t_R$, is also highlighted, and defined, as above, as the time centered on the return point in which grid movement slows down, stops, and resumes in the opposite direction with a comparable speed.

Finally, in reference to FIG. 7, in accordance with an embodiment of the invention, the profile of the amplitude of the displacement motion is displayed. In this instance the motion is derived from a triangular periodic pattern, although other patterns are possible and contemplated. Return point 1 of period 1 is altered with respect to return point 2 of period 2.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A mammograph comprising:
 a radiation source configured to emit radiation for taking mammographic images of a patient;
 a radiation detector comprising a network of sensors arranged periodically with a first pitch;
 an anti-scattering grid arranged between the source and the detector, the anti-scattering grid comprising radiation adsorbing strips arranged parallel to each other and distributed periodically with a second pitch; and
  at least one actuator configured to displace the anti-scattering grid relative to the detector or displace the detector relative to the anti-scattering grid during emission of radiation,
  wherein displacement is perpendicular to the direction of the strips of the anti-scattering grid, the strips being arranged parallel to a side of the anti-scattering grid positioned against the patient, and the locations of the return points are changed between successive cycles of the displacement motion.

2. The mammograph of claim 1, wherein the at least one actuator is configured to displace at least one of the anti-scattering grid and the detector in a manner derived from a periodic pattern where the velocity just before and just after the return point is higher than for an oscillation of same amplitude and frequency.

3. The mammograph of claim 1, wherein the at least one actuator comprises at least one of a stepper motor, electromagnet, voice coil, linear actuator, and piezoelectric motor.

4. The mammograph of claim 1 wherein the combined movements of both the anti-scattering grid and the detector relative to each other alter the perceived relative return point of the grid as viewed by the detector.

5. The mammograph of claim 1 comprising two actuators, wherein the two actuators comprise motors operating at speeds different to each other.

6. The mammograph of claim 1, wherein the at least one actuator is arranged on a side of the anti-scattering grid opposite the side of the grid positioned against the patient.

7. The mammograph of claim 1, wherein the second pitch is at least one of a multiple of the first pitch, and a multiple of the Nyquist frequency of the detector.

8. The mammograph of claim 1, further comprising a control and processing unit configured to control the source and the detector and configured to control acquisition and processing of images.

9. A process for deploying an anti-scattering grid in a mammograph comprising a radiation source configured to emit radiation for taking mammographic images of a patient, a radiation detector comprising a network of sensors arranged periodically with a first pitch, and an anti-scattering grid arranged between the source and the detector, the anti-scattering grid comprising radiation-adsorbing strips arranged parallel to each other and distributed periodically with a second pitch, the process comprising:
 displacing at least one of the anti-scattering grid relative to the detector and displacing the detector relative to the anti-scattering grid during emission of radiation;
 wherein displacement is perpendicular to the direction of the strips of the anti-scattering grid, the strips being arranged parallel to a side of the anti-scattering grid positioned against the patient, and the locations of the return points are changed between successive cycles of the displacement motion.

10. The process of claim 9, wherein the displacement motion is derived from a periodic pattern where the velocity just before and just after the return point is higher than for an oscillation of same amplitude and frequency.

11. The process of claim 9, wherein the periodic pattern is a triangular wave.

12. The process of claim 9, wherein the amplitude of the grid displacement is longer than 5 periods of the strips of the anti-scattering grids.

13. The process of claim 9, wherein the return time is smaller than 5% of the grid movement period.

14. The process of claim 9, wherein the amplitude of the displacement motion period to period is changed by at least one of a, random number generator, pseudo-random equation, and a complex periodic movement.

15. The process of claim 14, wherein the amplitude of the displacement motion period to period is altered in relation to exposure time.

16. The process of claim 9, wherein at least one of an electromagnet, linear motor, and voice coil are used to drive the displacement motion.

17. The process of claim 9, wherein the displacement motion profile is tailored to reduce the required acceleration of the anti-scattering grid for a given radiation emission duration.

18. The process of claim 9, wherein the displacement occurs in a space of 2 mm or less.

19. The process of claim 9, further comprising moving the source relative to the detector to acquire three-dimensional mammographic images.

20. The process of claim 9, wherein the first pitch of the detector is adapted to the second pitch of the scattering grid.

\* \* \* \* \*